(12) United States Patent
Eberhardt et al.

(10) Patent No.: US 11,654,022 B2
(45) Date of Patent: May 23, 2023

(54) STENTS FOR PROSTHETIC HEART VALVES AND METHODS OF MAKING SAME

(71) Applicant: Medtronic, Inc., Minneapolis, MN (US)

(72) Inventors: Carol E. Eberhardt, Fullerton, CA (US); Faisal Kalam, Corona, CA (US)

(73) Assignee: Medtronic, Inc., Minneapolis, MN (US)

( * ) Notice: Subject to any disclaimer, the term of this patent is extended or adjusted under 35 U.S.C. 154(b) by 312 days.

(21) Appl. No.: 16/916,756

(22) Filed: Jun. 30, 2020

(65) Prior Publication Data

US 2020/0383778 A1    Dec. 10, 2020

Related U.S. Application Data

(60) Continuation of application No. 15/388,022, filed on Dec. 22, 2016, now Pat. No. 10,729,540, which is a continuation of application No. 13/953,100, filed on Jul. 29, 2013, now Pat. No. 9,561,119, which is a division of application No. 12/714,757, filed on Mar. 1, 2010, now Pat. No. 8,500,801.

(60) Provisional application No. 61/171,193, filed on Apr. 21, 2009.

(51) Int. Cl.
| | |
|---|---|
| *A61F 2/24* | (2006.01) |
| *B21C 37/15* | (2006.01) |
| *B21D 31/00* | (2006.01) |
| *A61F 2/82* | (2013.01) |
| *B21C 37/06* | (2006.01) |

(52) U.S. Cl.
CPC .......... *A61F 2/2418* (2013.01); *A61F 2/2415* (2013.01); *A61F 2/82* (2013.01); *B21C 37/157* (2013.01); *B21D 31/00* (2013.01); *A61F 2210/0014* (2013.01); *A61F 2230/0023* (2013.01); *A61F 2230/0054* (2013.01); *A61F 2240/001* (2013.01); *B21C 37/065* (2013.01)

(58) Field of Classification Search
CPC .... A61F 2/2418; A61F 2/2415; B21C 37/065; B21D 31/00
See application file for complete search history.

(56) References Cited

U.S. PATENT DOCUMENTS

| | | |
|---|---|---|
| 1,942,353 A | 1/1934 | Kornel |
| 3,248,184 A | 4/1966 | Livesay et al. |
| 3,483,723 A | 12/1969 | Verkaik |
| 3,570,014 A | 3/1971 | Hancock |
| 3,845,903 A | 11/1974 | Runniger |
| 4,106,129 A | 8/1978 | Carpentier et al. |
| 4,532,793 A | 8/1985 | Bezold |
| 4,626,255 A | 12/1986 | Reichart |
| 4,685,321 A | 8/1987 | van den Berg et al. |
| 5,489,298 A | 2/1996 | Love et al. |
| 5,716,417 A | 2/1998 | Girard et al. |
| 5,904,697 A | 5/1999 | Gifford, III |
| 6,001,124 A | 12/1999 | Backinski |
| 6,245,102 B1 | 6/2001 | Jayaraman |

(Continued)

*Primary Examiner* — Brian A Dukert
(74) *Attorney, Agent, or Firm* — Michael Best & Friedrich LLP

(57) ABSTRACT

A single piece stent construction having a plurality of commissure posts, each of which extends upwardly from a solid ring along a bend line and generally along a central longitudinal axis of the stent.

15 Claims, 2 Drawing Sheets

(56) References Cited

U.S. PATENT DOCUMENTS

| | | |
|---|---|---|
| 6,425,916 B1 | 7/2002 | Garrison |
| 6,494,889 B1 | 12/2002 | Fleischman |
| 6,733,525 B2 | 5/2004 | Yang et al. |
| 7,100,416 B2 | 9/2006 | Suzumura |
| 7,220,275 B2 | 5/2007 | Davidson et al. |
| 7,267,680 B2 | 9/2007 | Wright |
| 7,270,679 B2 | 9/2007 | Istephanous et al. |
| 7,361,192 B2 | 4/2008 | Doty |
| 7,374,571 B2 | 5/2008 | Pease et al. |
| 7,399,315 B2 * | 7/2008 | Iobbi .................. A61F 2/2412 623/2.14 |
| 7,517,363 B2 | 4/2009 | Rogers et al. |
| 7,871,436 B2 | 1/2011 | Ryan et al. |
| 8,500,801 B2 | 8/2013 | Eberhardt et al. |
| 2003/0014104 A1 | 1/2003 | Cribier |
| 2003/0130726 A1 | 7/2003 | Thorpe et al. |
| 2003/0208261 A1 | 11/2003 | Thorpe et al. |
| 2004/0138737 A1 | 7/2004 | Davidson et al. |
| 2005/0267581 A1 | 12/2005 | Marnay et al. |
| 2006/0020341 A1 | 1/2006 | Schneid et al. |
| 2006/0173537 A1 | 8/2006 | Yang et al. |
| 2006/0271161 A1 | 11/2006 | Meyer |
| 2008/0109081 A1 | 5/2008 | Bao et al. |
| 2008/0215144 A1 | 9/2008 | Ryan |
| 2008/0249619 A1 | 10/2008 | Stacchino et al. |
| 2008/0255660 A1 | 10/2008 | Guyenot et al. |
| 2009/0005863 A1 | 1/2009 | Goetz |
| 2009/0062920 A1 | 3/2009 | Tauber |
| 2009/0082867 A1 | 3/2009 | Sebastian et al. |
| 2009/0132052 A1 | 5/2009 | Baccelli et al. |
| 2009/0223952 A1 | 9/2009 | Wnek |
| 2009/0248139 A1 | 10/2009 | Pellegrini |
| 2010/0049306 A1 | 2/2010 | House et al. |
| 2010/0049313 A1 | 2/2010 | Alon et al. |
| 2010/0256723 A1 | 10/2010 | Murray |
| 2011/0040374 A1 | 2/2011 | Goetz et al. |

\* cited by examiner

STENTS FOR PROSTHETIC HEART VALVES AND METHODS OF MAKING SAME

CROSS-REFERENCE TO RELATED APPLICATIONS

This application is a Continuation of and claims the benefit of U.S. patent application Ser. No. 15/388,022, filed Dec. 22, 2016, now allowed, which is a Continuation of and claims the benefit of U.S. patent application Ser. No. 13/953,100, filed Jul. 29, 2013, now U.S. Pat. No. 9,561,119, which is a Division of and claims the benefit of U.S. patent application Ser. No. 12/714,757, filed Mar. 1, 2010, now U.S. Pat. No. 8,500,801, which claims the benefit under 35 U.S.C. § 119(e) of U.S. Provisional Patent Application No. 61/171,193, filed Apr. 21, 2009, the disclosures of which are incorporated by reference in their entirety.

TECHNICAL FIELD

The present invention relates generally to stents for use with valves, and more particularly relates to stent frame constructions.

BACKGROUND

A wide variety of stent configurations and constructions are available for use with stented valves, such as stented heart valves. Many of these stents comprise wire or metal frames having a number of different components or sections that are arranged in a particular manner to provide certain characteristics for the finished device or component. For some applications, the stents can be made from shape memory materials, such as Nitinol, that can be compressed to a reduced size for implantation held in that compressed state, and then released to allow their expansion once they are positioned at a desired implantation site. In other applications, the stents can be compressed to a reduced size, and then expanded when desired through the use of an outward radial force that is applied from the inner area of the stent, such as can be accomplished with an expandable balloon. In still other applications, a stent used for a stented valve may not be compressible and expandable, but may instead have fixed dimensions. In many of these applications, the stents are provided with relatively cylindrical outer shapes to generally match the shape of the vessels in which they will be implanted.

One method of making a stent is to start with a tube or cylinder of material having solid walls and cutting out certain portions to provide apertures and/or other structural features for the stent. For example, removing large and/or multiple portions of material from a cylinder may be desirable to provide openings in certain areas of a stent while providing sufficient structure that will be conducive to compression for percutaneous delivery. However, it can be difficult to manufacture relatively large tubes that are made of materials such as Nitinol, and these tubes can therefore be expensive and difficult to find. Another method of making stents, such as stents having large diameters, is to use Nitinol wires arranged and attached to each other in predetermined patterns to make a particular structure. However, this method can be tedious and also requires crimping or welding wire ends to each other to form a cylinder, which can be very labor intensive. Yet another method of making stents involves using a flat sheet of material from which portions of material are removed. However, this method also requires the use of a weld seam to join the two ends of the flat sheet into a tubular stent. Although such constructions can be appropriate in some situations, it is also understood that weld seams can be the weakest point in a stented valve construction. Thus, it is desirable to provide additional methods for producing stents of various materials and may particularly be desirable to provide methods and configurations that do not require the use of welds or other attachment methods.

SUMMARY

The stent frames of the invention are generally provided for use with an attached valve structure to create a valved stent, which can be used as a replacement heart valve, for example. The stent frames are made from a single piece of material, thereby eliminating weld seams that can provide an undesirable area of weakness. The stents of the invention include a wide variety of structures and features that can be used alone or in combination with features of other stents of the invention.

Methods of forming the stent frames of the invention include cutting or stamping a stent blank from a sheet of material, or otherwise forming molding a stent blank that is relatively flat. The stent blank can then be formed into a cylinder shape using heat treatment in a stepwise method, thereby forming a tubular stent frame. Alternatively, the stent blank can be formed into a cylinder shape using a deep forming or shaping process to form a tubular stent frame. A bioprosthesis can be attached to the wires of this stent in certain, predetermined locations and preferably will be sewn to the wires in such a way that the material

BRIEF DESCRIPTION OF THE DRAWINGS

The present invention will be further explained with reference to the appended Figures, wherein like structure is referred to by like numerals throughout the several views, and wherein.

DETAILED DESCRIPTION

In accordance with the invention, forming methods are provided for use in stent construction. In particular, methods and constructions are provided that involve heat treatment for materials such as Nitinol and sheet metal deep forming for material such as stainless steel, and particularly involve the use of a single, integral stent construction involving these types of formation methods. With these embodiments, the methods and constructions of the invention eliminate the use of welds or other forms of attachment of components in the stent construction.

Figure 1:
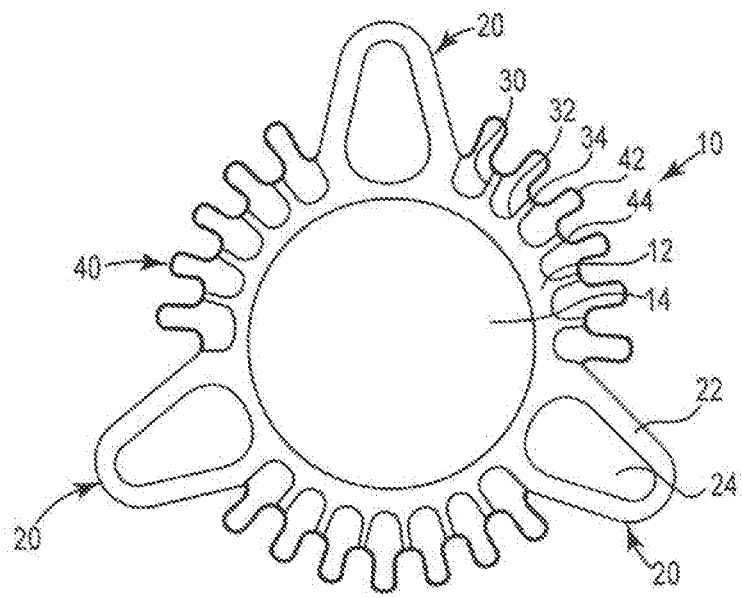
FIG. 1 is a top view of an embodiment of a stent blank having a first exemplary pattern.
Figure 2:
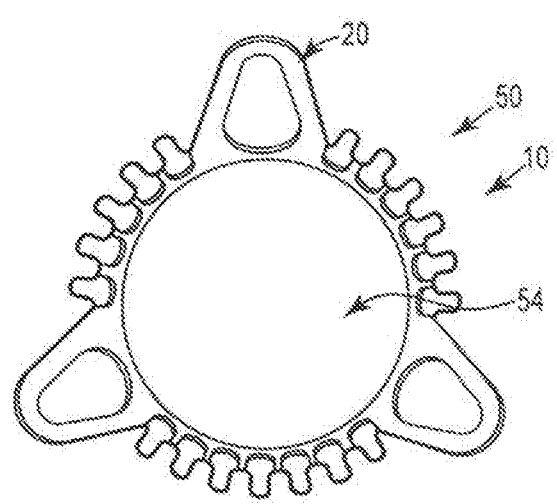
FIG. 2 is a top perspective view of the stent blank of FIG. 1 formed into a relatively cylindrical or tubular stent shape.

Referring initially to FIGS. 1 and 2, one exemplary heart valve stent design in accordance with the invention is illustrated. With this design, a stepwise heat treatment approach can be taken to form a stent from a flat sheet of material, such as a shape memory material (e.g., Nitinol). First, a flat sheet of material is provided and a predetermined shape for the stent is cut from the material, which can be accomplished with a stamping operation or by cutting the material with a laser, for example. As is shown in FIG. 1, a flat stent blank 10 includes a central ring 12 surrounding a generally circular opening 14, and three shaped members 20 that extend outwardly from the central ring 12.

In this embodiment, the shaped members 20 are spaced from each other at predetermined locations around the central ring, each of which can be used as one of the commissures for a valve, as will be explained below. These shaped members 20 are configured to have a generally teardrop or modified oval shape, although other shapes for the members are contemplated. In one embodiment, each of the members 20 is spaced at approximately 120 degrees from each adjacent member 20. However, it is contemplated that all of the members 20 are not evenly spaced from each other. Such a non-uniform spacing can be provided to accommodate for particular anatomical or other structural considerations for the formed stent structure and any valves or other structures that will be positioned in the internal stent area. It is further contemplated that more or less than three of such members are provided for a blank of the invention, where the resulting stent embodiments will have more or less than three commissure posts or segments and can thereby accommodate valves having more or less than three leaflets, for example.

Each of the members 20 comprises an outer frame 22 with an aperture 24 defined by an inner edge of the outer frame 22. These members 20 will provide the commissural posts for a stent frame after the forming process that will be described below. One or more of the members 20 can have a single aperture 24 that is generally teardrop shaped, although the aperture shape can be different, such as circular, oval, elliptical, triangular, rectangular, or the like. Each aperture 24 is shown as having the same relative size and shape for each of the members 20; however, the apertures 24 of a single frame can have different sizes and shapes from each other, such as can be provided to accommodate a certain configuration for the attachment of a valve within the interior area of the formed stent. One or more of the members 20 can alternatively be provided with multiple apertures that are spaced from each other in an ordered or random pattern across the face of the member. In a further alternative, one or more of the members 20 may be a solid piece that does not have any type of aperture.

The flat stent blank 10 further includes multiple support members 30 positioned between each pair of shaped members 20. In particular, each of the support members 30 extends outwardly at a first end 32 from the central ring 12 so that its second end 34 is spaced from the central ring 12 by a distance that is equal to the length of the support member 30. Each of the support members 30 is illustrated as a straight wire portion that extends at an angle of approximately 90 degrees relative to the outer edge surface of the central ring 12, although it is contemplated that the support members can be angled or curved relative to the central ring 12.

A sinusoidal wire structure 40 also extends between each adjacent pair of members 20 and is attached to or extends from the second end 34 of multiple support members 30. In particular, the sinusoidal wire structure 40 includes a series of peaks 42 and valleys 44, where the valleys 44 of the wire structure 40 are positioned at second end 34 of support members 30. Although the illustrated wire structure 40 is provided with the same number of valleys 44 as the number of support members 30 (i.e., every valley 44 corresponds with a support member 30 and vice versa), it is contemplated that there can be more or less valleys 44 on a particular wire structure than the number of support members 30 that extend from the central ring 12. In this embodiment of the invention, the overall distance that the shaped members 20 extend from the central ring 12 is larger than the overall distance that the support members and wire structure 40 extend from the central ring 12. However, it is understood that the relative sizes and shapes of the various components are only intended to be representative, and that the various portions of the stent blank 10 can be different from the illustrations.

The widths of the various components or members that make up the stent blank can be the same or different from each other. For example, the central ring 12 is shown as having a somewhat larger width than the support members 30 and wire structure 40. Such differences can be provided to allow deformation of certain portions of the stent blank 10 while maintaining other portions of the stent in a fixed configuration. In the embodiment of FIGS. 1 and 2, the wire structure 40 is has a relatively small width so that it can be reconfigured or deformed a particular amount during the stent forming process while allowing for a different amount of deformation of the central ring 12 during this same stent forming process.

FIG. 2 illustrates the flat blank 10 of FIG. 1 after it has been formed into a cylinder shape using heat treatment in a stepwise method to form a stent 50. That is, heat is applied to the flat piece of material in a manner that allows it to be formed into a cylinder, while still maintaining the material properties of the sheet. Such a heat treatment method might be used when the blank is made from a material such as Nitinol or another shape memory material; however, should the blank be made from a different material, such as stainless steel, a different heat treatment method may be used, such as deep forming. The various structures of the flat piece of material or blank can be heated to a sufficient temperature to allow it to be reconfigured without completely changing the shape or structure of the structures that make up the blank. That is, the shaped members 20, which will provide the commissure posts for a valve, are formed upwardly relative to the central ring 10 until the shaped members 20 are generally parallel to a central longitudinal axis that extends through the central ring 10. At the same time, the support members 30 and the corresponding wire structure 40 extending from the support members will also be formed upwardly relative to the central ring 10. The sinusoidal shape of the wire structure 40 advantageously allows for its deformation during the forming process to accommodate the positioning of the components. That is, the sides of the arches of the wire structure 40 can be moved toward or away from each other without significantly altering the overall shape of the stent 50.

In an alternative embodiment, one or more of the shaped members 20, support members 30, and/or wire structures 40 can be formed so that they at least slightly offset or angled relative to the central longitudinal axis of the formed stent. For example, one or more of the components can be slightly flared or angled outwardly relative to the longitudinal axis.

After the stent 50 is formed and cooled as described above, a valve structure can be positioned within its internal area 54. The valve can be attached in such a way that each of its commissures is attached to one of the shaped members 20. In one example, a valve structure can be sewn or adhered to the shaped members 20 in such a way that a leaflet extends between each adjacent pair of shaped members 20. In a particular example, valve tissue can be pulled through the openings 24 for attachment of the valve to the outer frame 22, where the tissue can optionally be wrapped or partially wrapped around the outer frame 22.

The illustrated shaped members 20, sinusoidal wire structures 40, and support members 30 of the stent structure 50 are only one exemplary embodiment of an arrangement that will provide sufficient structural support for the stent when it is formed into its cylindrical shape. That is, many other structures and shapes are considered to be within the scope of the invention that would also provide such support for the stent. For example, the central ring 12 can have a shape that is not circular, but instead is oval, elliptical, irregularly shaped, or the like, in order to accommodate different valve configurations, for example.

Figure 3:
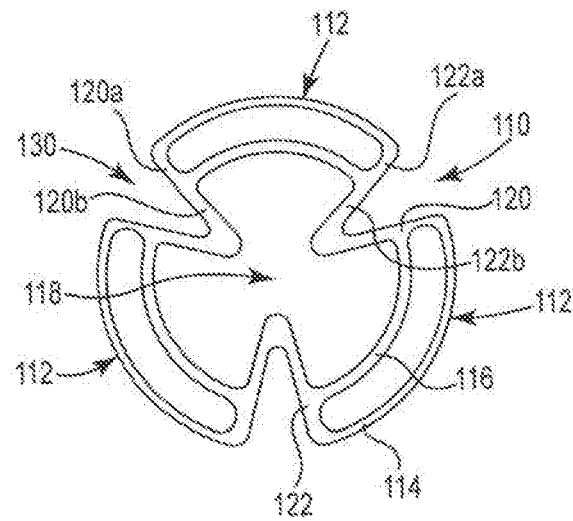
FIG. 3 is a top view of another embodiment of a stent blank having a second exemplary pattern.
Figure 4:
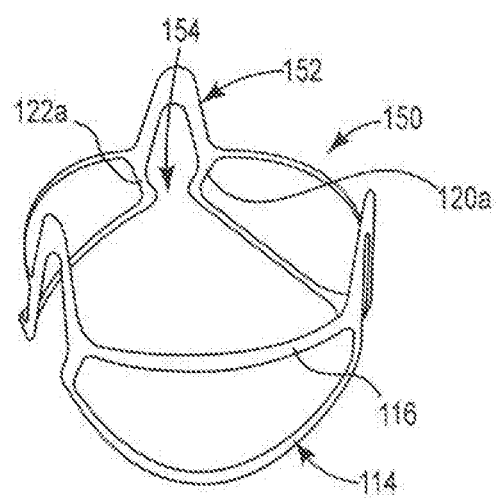
FIG. 4 is a perspective view of the stent blank of FIG. 3 formed into a relatively cylindrical or tubular stent shape.

Referring now to FIGS. 3 and 4, another exemplary heart valve stent design in accordance with the invention is illustrated. With this design, a deep forming process can be used to form a stent from a flat sheet of material, such as stainless steel. First, a flat sheet of material is provided and a predetermined shape for the stent is cut from the material, which can be accomplished with a stamping operation or by cutting the material with a laser, for example. As is shown in FIG. 3, a flat stent blank 110 includes three flanges 112, each of which includes a first arc portion 114 and a second arc portion 116 spaced from the first arc portion 114.

In this embodiment, each of the flanges 112 is defined by a first portion 114, which also defines a portion of the outer edge of the blank 110, a second portion 116 which is closer to a central area 118 of the blank 110 than the portion 114, a first edge 120 from which one end of the first and second portions 114, 116 extend, and a second edge 122 from which the other end of the first and second portions 114, 116 extend. That is, edges 120, 122 define the two sides of each flange 112, and the first and second arc portions 114, 116 extend between these edges 120, 122. Further, the edges 120, 122 are angled away from each other and the first portion 114 has a greater length than the second arc portion 116. Further, the flanges 112 are positioned about the central area 118 of the blank 110 so that one angled edge 120 of one flange 112 and one angled edge 122 of an adjacent flange 112 intersect to provide a V-shaped structure that defines a V-shaped space 130 between two adjacent flanges 112. In this embodiment, such a space 130 is provided between each pair of adjacent flanges 112 so that three V-shaped spaces are provided around the blank 110.

In this embodiment, each of the flanges 112 is spaced at approximately 120 degrees from each adjacent flange 112. Accordingly, each of the V-shaped spaces 130 is also spaced at approximately 120 degrees from each adjacent space 130. This spacing of the V-shaped spaces 130 can be defined with a radial line that is extended outwardly from the centerpoint of the blank 110 and through the base of each V-shaped space 130 such that the radial lines would each be spaced at 120 degrees from each other. However, it is contemplated that all of the flanges 112 are not evenly spaced from each other on a particular blank 110. Such a non-uniform spacing can be provided to accommodate for particular anatomical or structural features for the formed stent structure and/or any valves or other structures that will be positioned within the internal stent area, once a stent is formed. It is further contemplated that a blank is provided with more or less than three of such members, where such blanks will provide stent structures that have more or less than three commissures posts or segments, and can thereby accommodate valves having more or less than three leaflets.

As described and illustrated, each of the flanges 112 comprises two arc portions 114, 116; however, the flanges 112 can alternatively include more or less than two arc portions. It is further contemplated that the difference in lengths between the arc portions can be different than shown, which will thereby provide a different angle between the edges that define the V-shaped spaces 130. In addition, the entire length of each of the arc portions is not necessary a smooth curved shape having a generally uniform radius, as shown, but can instead comprise alternative shapes, such as multiple arcs connected to each other, one or more arcs connected to one or more straight portions, and the like.

Although the base of each V-shaped space is illustrated as an intersection point between two linear edge portions, other configurations are possible. For example, the base of one or more of the V-shaped spaces can include a radius or curved intersection area.

The angled edges 120, 122 may also be configured differently than illustrated. For example, these edges can be curved or otherwise configured to cooperate with the arc portions that extend between them. In another example, each of the edges can comprise a combination of one or more curved or straight portions that extend from each other along its length. It is noted that each of the edges 120, 122 includes a portion 120a, 122a, respectively that extends between the ends of two arc portions and another portion 120b, 122b, respectively, that extends from one arc portion to the base of the V-shaped space.

FIG. 4 illustrates the blank 110 of FIG. 3 after it has been formed into a cylinder shape using a deep forming or other metal forming/shaping process to form a stent 150. That is, the various structures of the blank 110 are shown after they have been deep formed in a process that allows the sheet to be shaped into a cylinder, while still maintaining the material properties of the sheet. Such a heat treatment method might be used when the blank is made from a material such as stainless steel; however, should the blank be made from a different material, such as Nitinol or another shape memory material, a different heat treatment method may be used. The various structures of the flat sheet can be formed in such a way that the V-shaped structures and/or flanges are extending in a direction that is generally parallel to a central longitudinal axis of the cylindrical stent. Alternatively, one or more of the structures of this stent can also be at least slightly offset or angled relative to the central longitudinal axis of the formed stent. After the stent is formed and cooled, a valve structure comprising leaflets can be attached within the interior portion of the stent, if desired.

The illustrated V-shaped structures, spoke portions, arc portions, etc. of the stent structure are only one exemplary embodiment of an arrangement that will provide sufficient structural support for the stent when it is formed into its cylindrical shape. Thus, many other structures and shapes can be provided that would also provide such support for the stent.

As illustrated in FIG. 4, the V-shaped structures extend upwardly in such a way that they create commissure posts 152 between each pair of arc portions 114, 116. The upper portion of each of these structures is defined by the edge portions 120b, 122b of two adjacent flanges 112, which are the edge portions that extend beyond the arc portions 116. One or more of the posts 152 may be defined partially by edge portion 120a and/or edge portion 122a that is bent or formed inwardly toward the opposite edge portion to create a space 154 between them. Alternatively, these edge portions can touch or almost touch, thereby creating an area for attachment or other cooperation with tissue or valve material. In yet another alternative, the edge portions 120a, 122a are generally in line with the other portions 120b, 122b of the edges 120, 122.

The present invention has now been described with reference to several embodiments thereof. The contents of any patents or patent application cited herein are incorporated by reference in their entireties. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A method of forming a tubular stent having a single-piece construction for a prosthetic heart valve, the method comprising:
    providing a generally flat stent blank including a plurality of flanges, wherein;
        each of the flanges defines a first edge member, a second edge member opposite the first edge member, and a first arc portion that defines a portion of an outer edge of the blank and extends between the first and second edge members,
        the first arc portions of circumferentially adjacent ones of the flanges are circumferentially spaced from one another,
        the first edge member of a first one of the flanges and the second edge member of a second one of the flanges extend from the corresponding, first arc portion and are directly connected to one another at a tip to define a V-shaped structure,
        the first edge member of the first one of the flanges and the second edge member of the second one of the flanges are free of direct connection to one another other than at the tip;
    applying heat to the stent blank while bending the stent blank to form a tubular stent having a plurality of commissure posts extending generally along a longitudinal axis of the tubular stent.

2. The method of claim 1, wherein the stent blank comprises a shape memory material.

3. The method of claim 1, wherein the stent blank comprises stainless steel.

4. The method of claim 1, wherein the step of applying heat includes deep forming the stent blank into a tubular shape.

5. The method of claim 1, wherein the step of providing a generally flat stent blank includes cutting the stent blank from a solid sheet of material.

6. The method of claim 1, wherein following the step of applying heat, the commissure posts project away from the first arc portions.

7. The method of claim 1, wherein the stent blank further defines a plurality of the V-shaped structures, and further wherein respective ones of the V-shaped structures are located between circumferentially-adjacent ones of the first arc portions.

8. The method of claim 7, wherein the step of applying heat include transitioning each of the V-shaped structures into a corresponding one of the commissure posts.

9. The method of claim 7, wherein each of the V-shaped structures defines a V-shaped space.

10. The method of claim 9, wherein the step of applying heat includes altering a shape of the V-shaped space of each of the V-shaped structures.

11. The method of claim 1, wherein a circumferential spacing between circumferentially adjacent ones of the first arc portions in the stent blank is greater than the circumferential spacing in the tubular stent.

12. The method of claim 1, wherein each of the flanges further includes a second arc portion located closer to a central area of the stent blank as compared to the corresponding first arc portion, and further wherein following the step of applying heat, the second arc portion is longitudinally spaced from the corresponding first arc portion.

13. The method of claim 12, wherein an arc length of the each of the first arc portions is greater than an arc length of each of the second arc portions.

14. The method of claim 12, wherein the stent blank further comprises a plurality of the V-shaped structures, and further wherein respective ones of the V-shaped structures are located between circumferentially-adjacent ones of the second arc portions.

15. The method of claim 14, wherein the step of applying heat include transitioning each of the V-shaped structures into a corresponding one of the commissure posts.

* * * * *